United States Patent
Vulhop et al.

(10) Patent No.: US 10,729,438 B2
(45) Date of Patent: Aug. 4, 2020

(54) HYBRID MECHANISM FOR ATTACHMENT OF AN ADJUNCT TO A SURGICAL INSTRUMENT

(71) Applicant: Ethicon LLC, Guaynabo, PR (US)

(72) Inventors: Prudence Vulhop, Cincinnati, OH (US); Michael J. Vendely, Lebanon, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 456 days.

(21) Appl. No.: 15/436,183

(22) Filed: Feb. 17, 2017

(65) Prior Publication Data
US 2018/0235630 A1   Aug. 23, 2018

(51) Int. Cl.
A61B 17/068 (2006.01)
A61B 17/072 (2006.01)
A61B 17/00 (2006.01)

(52) U.S. Cl.
CPC .. *A61B 17/07292* (2013.01); *A61B 17/07207* (2013.01); *A61B 2017/00004* (2013.01); *A61B 2017/00893* (2013.01); *A61B 2017/07257* (2013.01); *A61B 2017/07271* (2013.01); *A61B 2017/07285* (2013.01)

(58) Field of Classification Search
CPC .............. A61B 17/07207; A61B 17/068
USPC .................. 227/180.1, 176.1, 175.1
See application file for complete search history.

(56) References Cited

U.S. PATENT DOCUMENTS

| | | | |
|---|---|---|---|
| 5,441,193 A | * | 8/1995 | Gravener ......... A61B 17/07207 227/175.1 |
| 7,143,925 B2 | | 12/2006 | Shelton, IV et al. |
| 7,601,118 B2 | | 10/2009 | Smith et al. |
| 8,317,070 B2 | | 11/2012 | Hueil et al. |

(Continued)

FOREIGN PATENT DOCUMENTS

| | | |
|---|---|---|
| EP | 1621141 A2 | 2/2006 |
| EP | 2759267 A2 | 7/2014 |
| EP | 2939608 A1 | 11/2015 |

OTHER PUBLICATIONS

European Search Report for Application No. 18157195.1, dated Jun. 18, 2018. (9 Pages).

*Primary Examiner* — Praachi M Pathak
(74) *Attorney, Agent, or Firm* — Mintz Levin Cohn Ferris Glovsky and Popeo, P.C.

(57) ABSTRACT

A hybrid attachment mechanism is provided to attach an adjunct to an end effector jaw of a surgical instrument, such as a surgical stapler. The hybrid attachment mechanism can include at least two attachment mechanisms, each configured to inhibit at least one manner of detachment from the end effector jaw. A first attachment mechanism can be configured to inhibit vertical removal of the adjunct. A second attachment mechanism can be configured to inhibit sliding of the adjunct with respect to the jaw. A third attachment mechanism can be configured to inhibit curling of the adjunct upon itself. Each of the attachment mechanisms can operate in concert with the others, allowing the hybrid attachment mechanism to simultaneously inhibit multiple forms of adjunct detachment. The hybrid attachment mechanism can be further configured to decouple from the end effector jaw, permitting deployment of the adjunct at a treatment site.

14 Claims, 6 Drawing Sheets

(56) References Cited

U.S. PATENT DOCUMENTS

| | | | |
|---|---|---|---|
| 8,393,514 B2 | 3/2013 | Shelton, IV et al. | |
| 9,282,962 B2 * | 3/2016 | Schmid et al. | |
| 10,213,198 B2 * | 2/2019 | Aronhalt | A61B 17/068 |
| 2013/0214030 A1 * | 8/2013 | Aronhalt | A61B 17/0682 |
| | | | 227/176.1 |
| 2013/0221065 A1 | 8/2013 | Aronhalt et al. | |
| 2013/0256377 A1 | 10/2013 | Schmid et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351758 A1 | 12/2015 | Shelton, IV et al. | |
| 2016/0089142 A1 | 3/2016 | Harris et al. | |
| 2017/0055986 A1 | 3/2017 | Harris et al. | |

\* cited by examiner

HYBRID MECHANISM FOR ATTACHMENT OF AN ADJUNCT TO A SURGICAL INSTRUMENT

FIELD

The present disclosure relates generally to hybrid mechanisms for attachment of an adjunct to a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Surgical stapling device adjuncts, devices, and methods are provided. In one embodiment, a surgical stapling device is provided and includes an elongate shaft having an end effector with first and second jaws configured to grasp tissue therebetween. The surgical stapling device further includes an adjunct disposed on a tissue contacting surface of one of the first and second jaws. The adjunct can be coupled to the jaw by a first attachment mechanism configured to maintain the adjunct on the tissue contacting surface, a second attachment mechanism configured to prevent lateral and longitudinal sliding of the adjunct along the tissue contacting surface, and a third attachment mechanism configured to prevent a distal end of the adjunct from separating from a distal-most end of the tissue contacting surface of the jaw.

The first, second, and third attachment mechanisms can have a variety of configurations. In one embodiment, the first attachment mechanism includes an adhesive that adheres the adjunct to the tissue contacting surface of the jaw. The second attachment mechanism can include at least one of a post or a bore formed on the adjunct and configured to mate with at least one of a corresponding post or bore formed on the tissue contacting surface of the jaw. The at least one post and bore can be configured to prevent longitudinal and lateral sliding of the adjunct relative to the tissue contacting surface. The third attachment mechanism can include a clip coupled to a distal-most end of the jaw and extending over the adjunct to prevent the distal end of the adjunct from separating from the distal-most end of the tissue contacting surface of the jaw. The clip can be configured to decouple from the distal-most end of the jaw to permit the distal end of the adjunct to separate from the distal-most end of the tissue contacting surface of the jaw.

In other aspects, the adjunct can include a first adjunct disposed on the tissue contacting surface of the first jaw, and the surgical stapling device can further include a second adjunct disposed on the tissue contacting surface of the second jaw.

In another embodiment, a surgical stapling device is provided and includes an elongate shaft having an end effector with first and second jaws configured to grasp tissue therebetween. The surgical stapling device can also include an adjunct disposed on a tissue contacting surface of one of the first and second jaws. An adhesive can maintain the adjunct on the tissue contacting surface. One of the adjunct and the tissue contacting surface of the jaw can include one or more posts formed thereon that are received within respective corresponding bores formed in the other one of the adjunct and the tissue contacting surface of the jaw. The surgical stapling device can also include a clip that extends over a distal-most end of the adjunct and that is secured to a distal-most end of the jaw to prevent curling of the distal-most end of the adjunct.

In certain aspects, the adhesive can be disposed between the tissue contacting surface and the adjunct. In one embodiment, the bore can have a diameter that is greater than a diameter of the post. The at least one post can be formed proximal to the portion of the adjunct over which the clip extends. In other embodiments, the clip can be configured to apply a compressive force to the distal-most end of the adjunct when secured to the distal-most end of the jaw. The surgical stapling device can further include a firing system configured to eject one or more staples through the adjunct. The clip can be configured to disengage from the distal-most end of the adjunct upon ejection of a staple. For example, the surgical stapling device can include a cutting element configured to cut tissue grasped between the first and second jaws during ejection of the one or more staples. The cutting element can disengage the clip from the distal-most end of the adjunct. In other aspects, the at least one post can be formed lateral to the clip, along the length of the end effector, when the clip is secured to the distal-most end of the jaw.

In another embodiment, a surgical stapling device is provided having an elongate shaft with an end effector with first and second jaws configured to engage tissue therebetween. An adjunct can be disposed on a tissue-contacting surface of one of the first and second jaws. A primary attachment mechanism can secure the adjunct to the jaw, and a secondary attachment mechanism can prevent deformation of a distal end of the adjunct proximate thereto.

In one embodiment, the primary attachment mechanism can inhibit in-plane sliding of the adjunct with respect to the tissue contacting surface of the jaw. In another embodiment, the primary attachment mechanism can be configured to adhere the adjunct to the tissue contacting surface of the jaw. In yet another embodiment, the secondary attachment mechanism can inhibit out-of-plane deformation of the adjunct with respect to the tissue contacting surface of the jaw. In other aspects of the surgical stapling device, the secondary attachment mechanism can be reversibly secured to the end effector such that removal of the secondary attachment mechanism from the end effector permits deformation of the distal end of the adjunct. The secondary attachment mechanism can exert a compressive force upon the distal end of the adjunct when secured to the end effector.

BRIEF DESCRIPTION OF DRAWINGS

This invention will be more fully understood from the following detailed description taken in conjunction with the accompanying drawings, in which.

DETAILED DESCRIPTION

Figure 1:
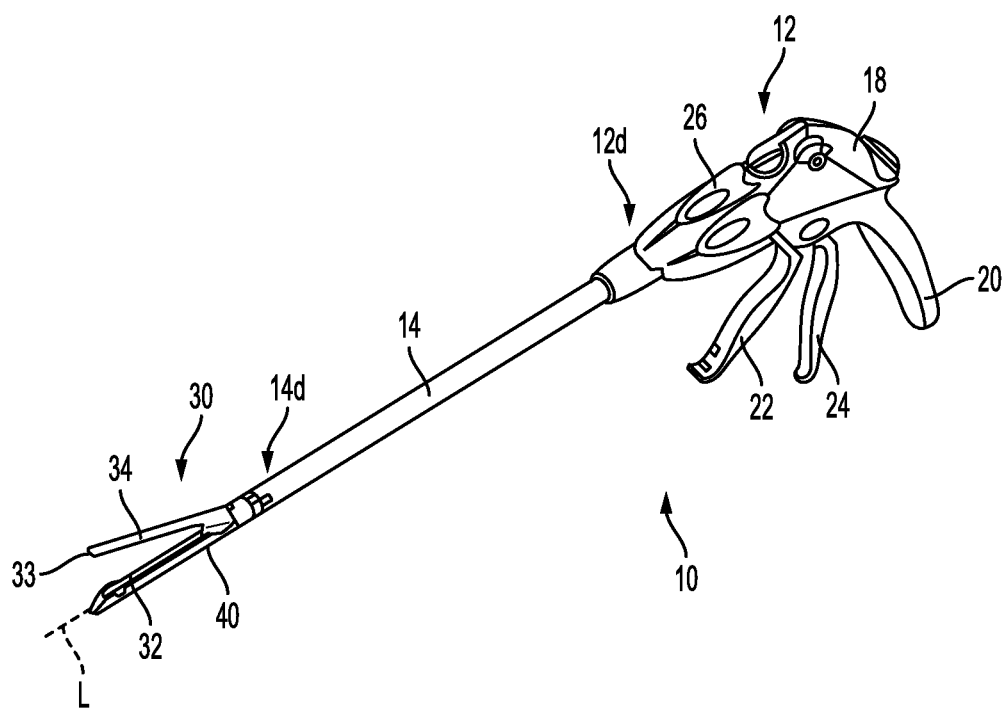
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein.

"Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
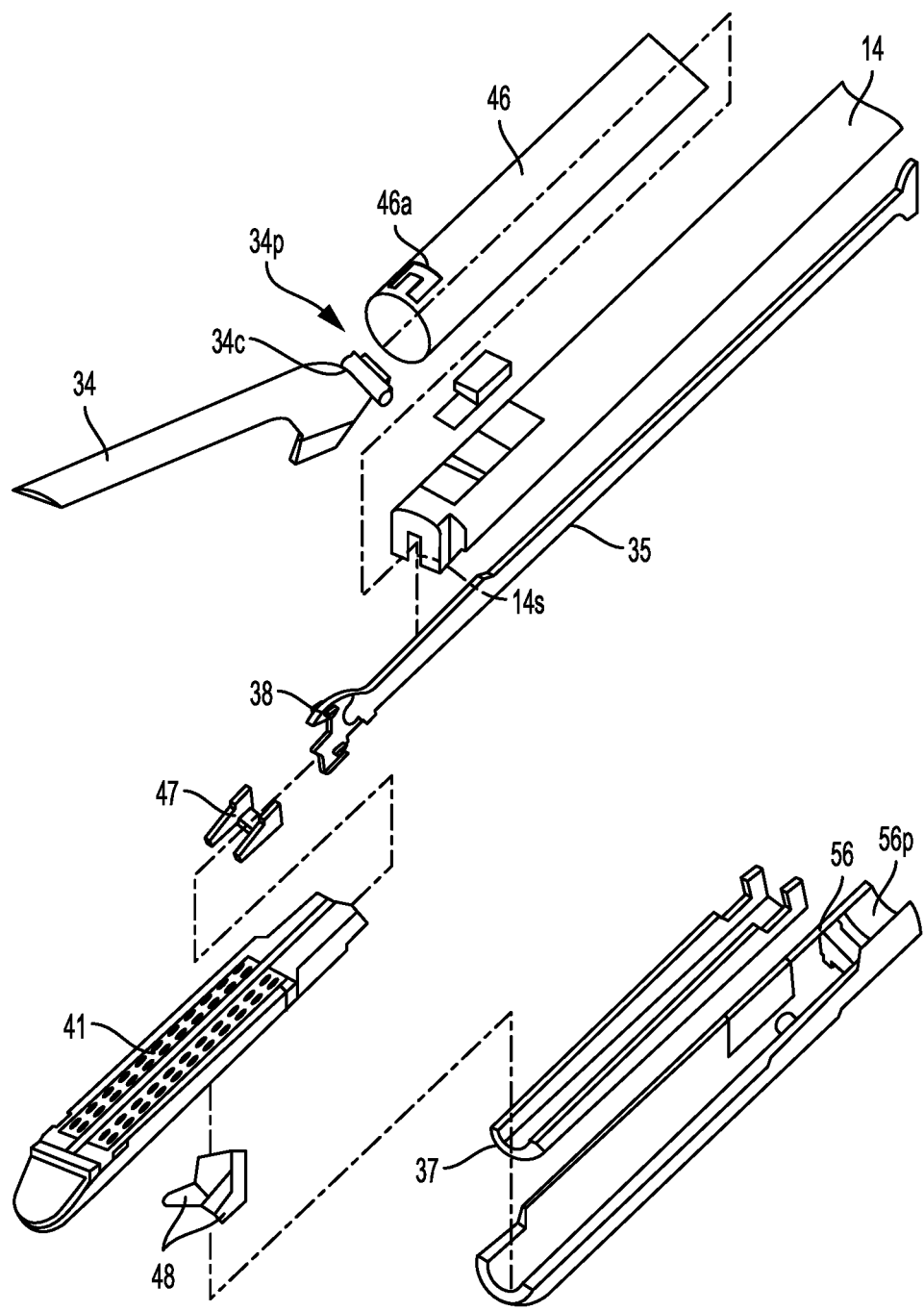
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue there between. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
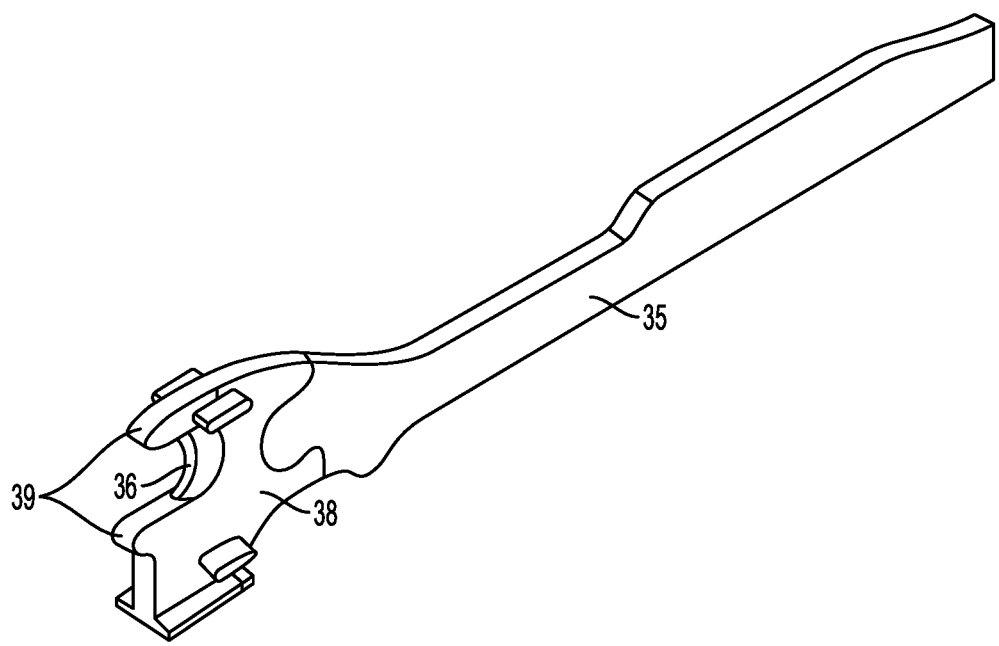
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife blade 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
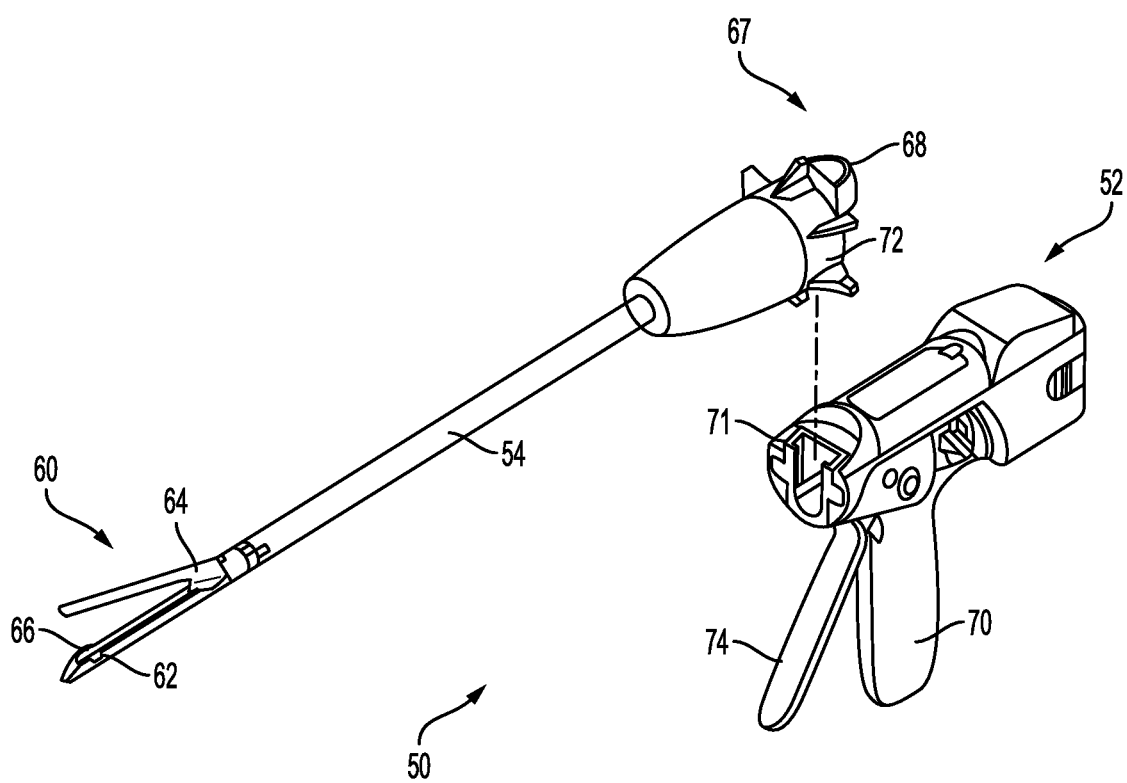
FIG. 4 is a perspective disassembled view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

In further embodiments, the surgical instrument can adopt other forms. In one example, the surgical instrument is in the form of a circular surgical stapler (not shown). The circular stapler can generally be configured and used similar to the linear staplers 10, 50 of FIGS. 1 and 4, but with some features accommodating its functionality as a circular stapler, such as a cartridge assembly configured to deploy staples against a circular anvil o form a circular pattern of staples, e.g., staple around a circumference of a tubular body organ.

The illustrated examples of surgical stapling instruments 10, 50 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/

0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction), such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

In general, when using an adjunct in conjunction with a surgical stapler, the adjunct can be removably attached to the end effector. The adjunct will preferably remain secured to the end effector while the end effector is positioned at a treatment site, and is removed from the end effector when staples are deployed at the treatment site to provide the benefits discussed above.

It has been observed that adjuncts can prematurely detach from the end effector prior to staple deployment. Detachment of the adjunct from the end effector can occur in various forms, depending on the manner in which the end effector is used. For example, detachment can include vertical lift off of the adjunct from the end effector, lateral sliding of the adjunct with respect to the end effector, and/or curling of the edges of the adjunct from the surface of the end effector. The adjunct could also slide sideways when an end effector is used to clamp and twist tissue.

Various exemplary devices, systems, and methods for attaching an adjunct to a surgical instrument are described herein. In general, a hybrid attachment mechanism is employed to attach an adjunct to an end effector jaw of a surgical stapler. In some embodiments, the hybrid attachment mechanism includes at least two attachment mechanisms, where each mechanism is configured to inhibit at least one form of adjunct detachment from the end effector jaw. For example, a first attachment mechanism can be configured to inhibit vertical removal of the adjunct from the jaw. A second attachment mechanism can be configured to inhibit sliding of the adjunct with respect to the jaw. A third attachment mechanism can be configured to inhibit curling of the adjunct upon itself. Each of the first, second, and third attachment mechanisms can operate in concert with the others, allowing the hybrid attachment mechanism to simultaneously inhibit multiple forms of adjunct detachment. The hybrid attachment mechanism can be further configured to decouple from the end effector jaw, permitting deployment of the adjunct at a treatment site.

Embodiments of the hybrid attachment mechanism are discussed below in conjunction with the stapler 10, where an adjunct is coupled to a tissue contacting surface 33 of the upper jaw 34 of an end effector 30. However, it may be understood that embodiments of the hybrid attachment mechanism can be employed with any surgical instrument without limit. Furthermore, embodiments of the hybrid attachment mechanism can be employed to couple adjuncts with the tissue contacting surface 33 of the upper jaw 34, a tissue contacting surface of the lower jaw 32, and combinations thereof.

Figure 5:
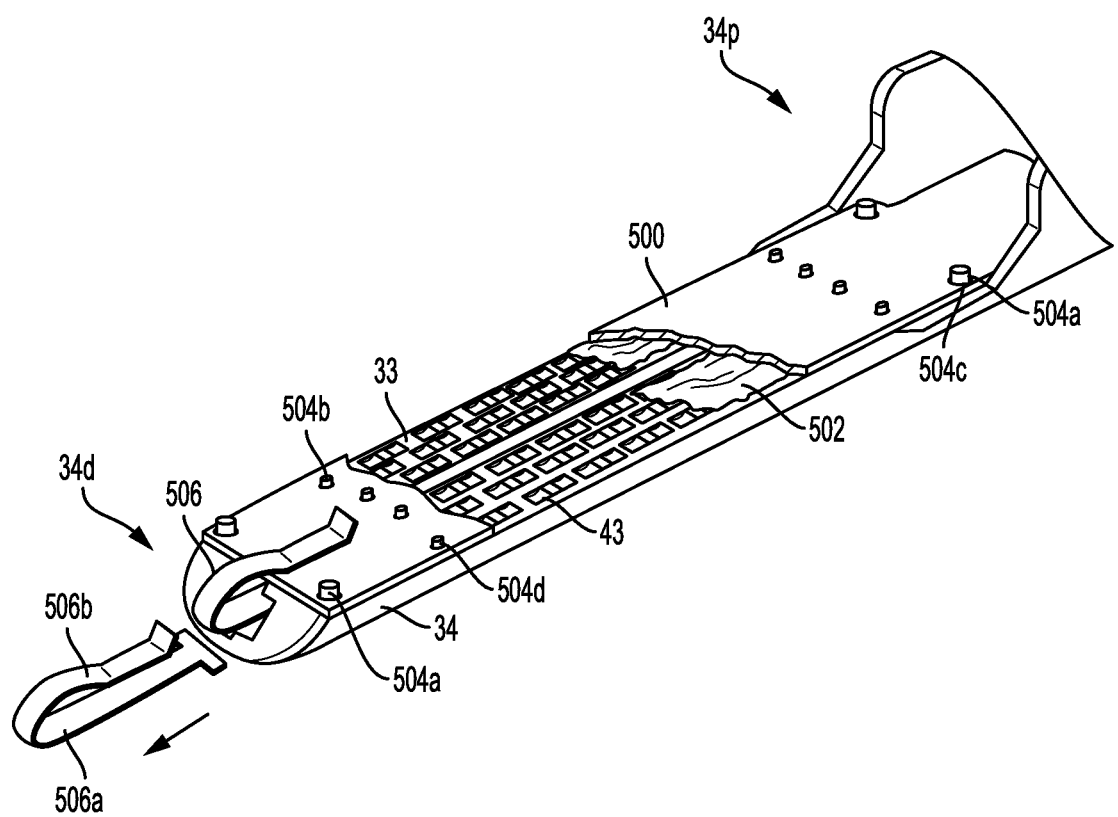
FIG. 5 is a perspective view of one embodiment of an adjunct coupled to an end effector jaw by a hybrid attachment mechanism.
Figure 6:
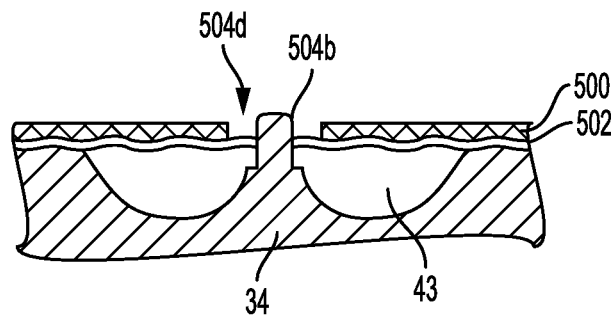
FIG. 6 is a cross-sectional view of the end effector jaw of FIG. 1, showing a portion of the adjunct of FIG. 5 coupled thereto.
Figure 7:
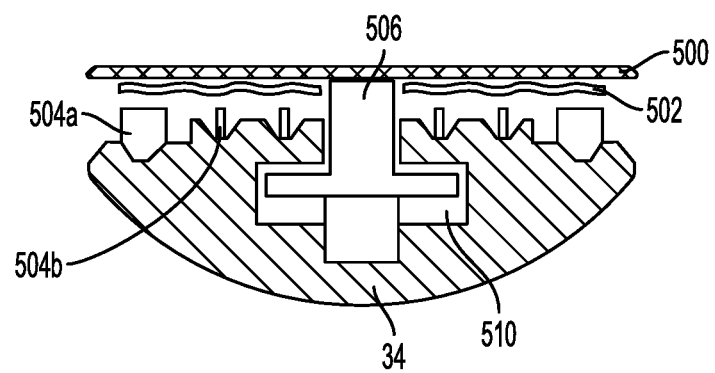
FIG. 7 is another cross-sectional view of the end effector jaw of FIG. 1, showing a portion of the adjunct of FIG. 5 coupled thereto.

FIGS. 5-7 show an adjunct 500 disposed upon a tissue contacting surface 33 (an anvil surface) of an upper jaw 34 including staple forming pockets 43 and a hybrid attachment mechanism configured to couple the adjunct 500 to the tissue contacting surface 33. The hybrid attachment mechanism includes a first attachment mechanism 502, a second attachment mechanism 504, and a third attachment mechanism 506.

In one embodiment, the first attachment mechanism 502 can be configured to maintain the adjunct 500 on the tissue contacting surface 33. For example, the first attachment mechanism 502 can be configured to inhibit out-of-plane deformation of the adjunct 500 and prevent vertical removal of the adjunct 500 from the tissue contacting surface 33. In a specific embodiment, the first attachment mechanism can be an adhesive 502 (e.g., a biocompatible adhesive) that adheres the adjunct 500 to the tissue contacting surface 33. As illustrated in FIGS. 5-7, the adhesive 502 is disposed between the tissue contacting surface 33 and the adjunct 500. Adhesives can include, but are not limited to, pressure sensitive adhesives (PSAs), heat activated adhesives, heat softened adhesives, ultraviolet (UV) cured adhesives, cyanoacrylate-based adhesives, moisture-softened adhesives, and hydrogel-based adhesives.

Mechanical properties of the adhesive 502 can be selected within ranges suitable to ensure that out-of-plane deformation of the adjunct 500 is inhibited during placement of the surgical stapling device 10 at a treatment site and that the adjunct 500 is released from the tissue contacting surface 33 when secured to tissue by one or more staples. Examples of suitable mechanical properties can include, but are not limited to, adhesion strength (peak load) and load-displacement response. These mechanical properties can be measured by one or more mechanical tests including, but not limited to, tension, compression, peel (90°, 180°, T), release force, loop tack, shear, and flexure performed at service temperatures (e.g., within the range between about room temperature and body temperature).

While the first attachment mechanism 502 can act to inhibit out-of-plane deformation, it may fail to prevent in-plane deformation. For example, the adhesive 502 can stretch longitudinally in response to applied in-plane tensile stresses, such as when sliding on tissue or when the knife (e.g., knife 36) is fired. As a result, at least a portion of the applied in-plane tensile stress can be felt by the adjunct 500 and can cause longitudinal elongation of the adjunct 500.

Accordingly, in another embodiment, the second attachment mechanism 504 can be configured to inhibit in-plane (e.g., lateral and/or longitudinal) sliding or deformation of the adjunct 500 along the tissue contacting surface 33. In one embodiment, the second attachment mechanism 504 can include at least one post 504a formed on one of the adjunct 500 and the tissue contacting surface 33 and a corresponding bore 504b formed on the other one of the adjunct 500 and the tissue contacting surface 33 that is configured to receive its corresponding post 504a. For example, the bore 504b can have a diameter less than, greater than, or approximately equal to that of the post 504a (FIG. 6). By combining the first attachment mechanism 502 and the second attachment mechanism 504, improved resistance to in-plane sliding or deformation is provided by the hybrid attachment mechanism.

In order to tailor the degree of resistance to in-plane sliding or deformation, the number of posts 504a, the size of the posts 504a, and their relative position with respect to the tissue contacting surface 33 can be varied. For example, as illustrated in the embodiment of FIGS. 5-7, multiple posts 504a, 504b are formed on the tissue contacting surface 33 and multiple respective bores 504c, 504d are formed on the adjunct 500. The posts 504a have a relatively larger diameter than the posts 504b and are positioned adjacent to the proximal end 34p and distal end 34d of the jaw 34. As further illustrated in the embodiment of FIG. 5, the number of posts 504b can be greater than the number of posts 504a. In this configuration, the posts 504a can act to inhibit sliding of the corners of the adjunct 500, while the posts 504b can act to inhibit stretching of the adjunct 500 along its length.

Under certain circumstances, ability of the first attachment mechanism 502 or the second attachment mechanism alone to prevent the adjunct 500 from curling upon itself can be impaired in service. For example, in the context of the first attachment mechanism 502, mechanical stresses experienced by the adjunct 500 or the jaw 34 can overcome the adhesion strength of the adhesive. Alternatively, in the context of the second attachment mechanism 504, mechanical stresses experienced by the adjunct 500 or the jaw 34 can damage the posts 504a. In either case, the ability of the first attachment mechanism 502 or the second attachment mechanism 504 to prevent the adjunct 500 from curling upon itself can be overcome. Furthermore, it is observed that curling of the adjunct 500 tends to occur most frequently at the distal end 34p of the jaw 34 because the distal end 34p of the jaw can frequently experience elevated stresses due to contact with tissue during use of the end effector 30.

Thus, in another embodiment, the third attachment mechanism 506 can be configured to inhibit in-plane movement or deformation of the adjunct 500 near a distal end of the jaw 34. Assuming the adjunct 500 possesses an in-plane area that is approximately the same as the area of the tissue contacting surface 33, the third attachment mechanism 506 can be configured to inhibit in-plane movement or deformation of a distal end of the adjunct 500 proximate to the tissue contacting surface 33. For example, the third attachment mechanism 506 can be configured to apply a compressive force to a distal-most end of the adjunct 500 when secured to a distal-most end of the jaw 34.

As illustrated in the embodiment of FIGS. 5 and 7, in one embodiment, the third attachment mechanism 506 can be a clip that reversibly couples to the jaw 34 to selectively permit or inhibit separation of the distal end of the adjunct 500 from the distal-most end of the tissue contacting surface 33. The illustrated clip includes a base 506a connected to an arm 506b. The illustrated clip is formed in a "U" or hook shape, with the arm 506b overlying the base 506a. A socket 510 can be formed in the distal-most end of the jaw 34 and extends longitudinally inward therefrom and is dimensioned to receive the base 506a. When the illustrated clip is coupled to the jaw 34, the arm 506b extends over the adjunct 500 and can exert the compressive force upon distal-most end of the adjunct 500. This compressive force prevents the distal end of the adjunct 500 from separating from the distal-most end of the tissue contacting surface 33. By varying the separation of the base 506a and the arm 506b, and/or an elastic modulus of the clip, the compressive force can be varied. Alternatively, when the base 506a of the clip is removed from the socket 510, the arm 506b of the clip does not extend over the adjunct 500 and does not exert the compressive force upon distal-most end of the adjunct 500, allowing separation of the distal-most end of the adjunct 500 from the tissue contacting surface 33.

The third attachment mechanism 506 can be configured to decouple from the jaw 34 upon ejection of a staple by the firing system. For example, as illustrated in FIGS. 5 and 7, the base 506a can be aligned with a path of the knife blade 36. When the firing system is activated, the staples are ejected from the staple cartridge 40 and the knife blade 36 is advanced through the jaw 34. The advancement of the knife blade 36 can be sufficient to push the base 506a out of the socket 510, decoupling the third attachment mechanism 506 from the jaw 34.

The third attachment mechanism 506 can be further configured to operate in combination with the second attachment mechanism 504. For example, as illustrated in the embodiment of FIG. 5, at least one post 504a is formed proximal to the portion of the adjunct 500 over which the arm 506b extends and applies the compressive force. That is, when the clip is coupled to the jaw 34, the arm 506b does not overlie any of the posts 504a. Thus, the posts 504a do not interfere with application of the compressive force to the adjunct 500 by the arm 506b. Furthermore, in addition to preventing curling of the adjunct 500 at the distal-most end of the adjunct 500, the compressive force exerted by the arm 506b upon the adjunct 500 can also act to inhibit in-plane sliding or deformation (longitudinally or laterally) of the distal end of the adjunct 500.

Figure 8:
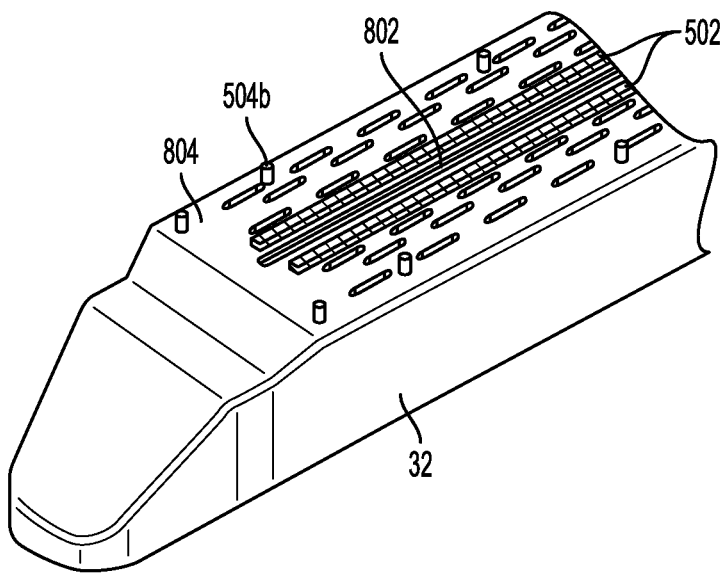
FIG. 8 is a perspective view of another embodiment of an adjunct coupled to an end effector jaw of FIG. 1.
Figure 9:
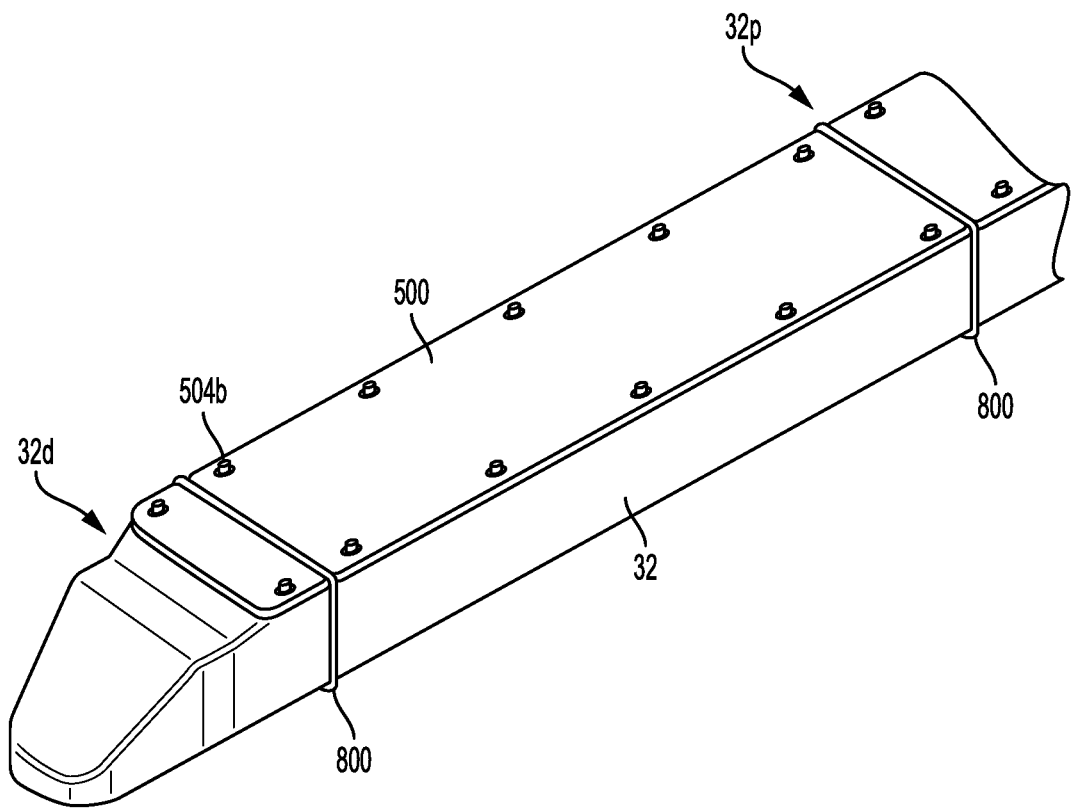
FIG. 9 is another perspective view of another embodiment of an adjunct coupled to an end effector jaw of FIG. 1.

FIGS. 8 and 9 illustrate another embodiment of a hybrid attachment mechanism configured for use with the stapler 10 and coupling the adjunct 500 to a tissue contacting surface of the jaw 32. However, it may be understood that embodiments of the hybrid attachment mechanism can be employed with any surgical instrument without limit. Furthermore, embodiments of the hybrid attachment mechanism can be employed to couple adjuncts with the tissue contacting surface 33 of the upper jaw 34, a tissue contacting surface of the jaw 32, and combinations thereof.

The hybrid attachment mechanism can include the first attachment mechanism 502, the second attachment mechanism 504, and a fourth attachment mechanism 800. As illustrated in FIG. 8, the first attachment mechanism 502 is provided in the form of longitudinal strips adjacent to a slot 802 that receives the knife 36 and the second attachment mechanism 504 is provided in the form of the posts 504a and/or 504b are arranged along the length of the jaw 32, adjacent the lateral sides.

FIG. 9 illustrates the fourth attachment mechanism 800 in combination with the adjunct 500. The fourth attachment mechanism 800 includes sutures that encircle a periphery of the jaw 32. For example, two sutures are positioned adjacent to a proximal end 32p and a distal end 32d of the jaw 32. However, any number of sutures can be provided and their location can be varied, as necessary. The sutures are configured to exert a compressive force upon the adjunct 500, inhibiting longitudinal and/or lateral sliding of the adjunct 500 with respect to the jaw 32, as well as vertical separation of the adjunct 500 with respect to the jaw 32. Thus, by combining the first attachment mechanism 502, the second attachment mechanism 504, and the fourth attachment mechanism 800, the hybrid attachment mechanism can provide improved resistance to out-of-plane deformation, maintaining the adjunct 500 is on the tissue contacting surface 804, as well as improving resistance to in-plane sliding or deformation.

In further embodiments, the fourth attachment mechanism 800 can be configured to decouple from the jaw 32 to permit the adjunct 500 to separate from the jaw 32. For example, the sutures extend laterally across the width of the jaw 32, intersecting the slot 802. When the firing system is activated, staples are ejected from the staple cartridge 40 and the knife blade 36 is advanced through the jaw 32 within the slot 802. The advancement of the knife blade 36 cuts the sutures, decoupling the third attachment mechanism 506 from the jaw 34.

It may be understood that, while embodiments of the hybrid attachment mechanism discussed above include the first attachment mechanism 502, the second attachment mechanism 504, and the third attachment mechanism 506, alternative embodiments of the hybrid attachment mechanism can include any two of the first attachment mechanism 502, the second attachment mechanism 504, the third attachment mechanism 506, and the fourth attachment mechanism 800. For example, the hybrid attachment mechanism can include the first attachment mechanism 502 and the second attachment mechanism 504, without the third attachment mechanism 506. Alternatively, the hybrid attachment mechanism can include the first attachment mechanism 502 and the third attachment mechanism 506, without the second attachment mechanism 504. Additionally, the hybrid attachment mechanism can include the second attachment mechanism 504 and the third attachment mechanism 506, without the first attachment mechanism 502. Alternatively, the hybrid attachment mechanism can include the first attachment mechanism 502 and the fourth attachment mechanism 800.

Terminology

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

A person skilled in the art will appreciate that the present invention has application in conventional minimally-invasive and open surgical instrumentation as well application in robotic-assisted surgery. In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Re-Use

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A surgical stapling device, comprising:
   an elongate shaft having an end effector with first and second jaws configured to grasp tissue therebetween;
   an adjunct disposed on a tissue contacting surface of one of the first and second jaws, the adjunct being coupled to the jaw by a first attachment mechanism configured to maintain the adjunct on the tissue contacting surface, a second attachment mechanism configured to prevent lateral and longitudinal sliding of the adjunct along the tissue contacting surface, and a third attachment mechanism configured to prevent a distal end of the adjunct from separating from a distal-most end of the tissue contacting surface of the jaw; and
   a cutting element configured to translate along the first and second jaws to cut tissue grasped therebetween and to push the third attachment mechanism off the jaw in a distal direction to permit the distal end of the adjunct to separate from the distal-most end of the tissue contacting surface of the jaw.

2. The surgical stapling device of claim 1, wherein the first attachment mechanism comprises an adhesive that adheres the adjunct to the tissue contacting surface of the jaw.

3. The surgical stapling device of claim 1, wherein the second attachment mechanism comprises at least one of a post or a bore formed on the adjunct and configured to be received in a corresponding post or bore formed on the tissue contacting surface of the jaw, the post and bore being configured to prevent longitudinal and lateral sliding of the adjunct relative to the tissue contacting surface.

4. The surgical stapling device of claim 1, wherein the third attachment mechanism comprises a clip coupled to a distal-most end of the jaw to prevent the distal end of the adjunct from separating from the distal-most end of the tissue contacting surface of the jaw, a first free terminal end of the clip being seated in a socket formed in the distal-most end of the jaw and a second free terminal end of the clip being positioned over the adjunct.

5. The surgical stapling device of claim 1, wherein the adjunct comprises a first adjunct disposed on the tissue contacting surface of the first jaw, and the surgical stapling device further includes a second adjunct disposed on the tissue contacting surface of the second jaw.

6. A surgical stapling device, comprising:
   an elongate shaft having an end effector at its distal end with first and second jaws configured to grasp tissue therebetween;
   an adjunct disposed on a tissue contacting surface of one of the first and second jaws, wherein an adhesive maintains the adjunct on the tissue contacting surface, one of the adjunct and the tissue contacting surface of the jaw includes one or more posts formed thereon that are received within respective corresponding bores formed in the other one of the adjunct and the tissue contacting surface of the jaw, and
   a U-shaped clip that extends over a distal-most end of the adjunct and is secured to a distal-most end of the jaw to prevent curling of the distal-most end of the adjunct, the U-shaped clip being disposed in a distal-facing opening that is formed in the jaw.

7. The surgical stapling device of claim 6, wherein the adhesive is disposed between the tissue contacting surface and the adjunct.

8. The surgical stapling device of claim 6, wherein, prior to receipt of a post within its corresponding bore, the bore has a diameter greater than a diameter of the post.

9. The surgical stapling device of claim 6, wherein the U-shaped clip is configured to apply a compressive force to the distal-most end of the adjunct when secured to the distal-most end of the jaw.

10. The surgical stapling device of claim 6, further comprising a firing system configured to eject one or more staples through the adjunct, wherein the U-shaped clip is configured to disengage from the distal-most end of the adjunct upon ejection of a staple.

11. The surgical stapling surgical stapling device of claim 10, further comprising a cutting element configured to cut tissue grasped between the first and second jaws during ejection of the one or more staples, wherein the cutting element disengages the U-shaped clip from the distal-most end of the adjunct.

12. The surgical stapling device of claim 6, wherein at least one post is formed proximal to the portion the distal-most end of the adjunct over which the U-shaped clip extends.

13. The surgical stapling device of claim 6, wherein at least one post is formed lateral to the U-shaped clip, along the length of the end effector, when the U-shaped clip is secured to the distal-most end of the jaw.

14. The surgical stapling device of claim 6, wherein the surgical stapling device further comprises a firing bar configured to translate within the elongate shaft to cause ejection of staples into tissue engaged between the jaws, the firing bar being configured to push the U-shaped clip out of the distal-facing opening during the translation of the firing bar.

* * * * *